(12) United States Patent
You et al.

(10) Patent No.: US 11,071,578 B2
(45) Date of Patent: *Jul. 27, 2021

(54) METHOD AND APPARATUS TO ELECTROCHEMICALLY TREAT ADIPOSE TISSUE IN THE HUMAN BODY

(71) Applicant: THE REGENTS OF THE UNIVERSITY OF CALIFORNIA, Oakland, CA (US)

(72) Inventors: Joon S You, Laguna Niguel, CA (US); Brian Jet-Fei Wong, Irvine, CA (US); Wesley Moy, Irvine, CA (US); Michael G. Hill, Pasadena, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 585 days.

This patent is subject to a terminal disclaimer.

(21) Appl. No.: 15/898,459

(22) Filed: Feb. 17, 2018

(65) Prior Publication Data

US 2018/0289413 A1    Oct. 11, 2018

Related U.S. Application Data

(63) Continuation-in-part of application No. 15/841,213, filed on Dec. 13, 2017, now Pat. No. 10,939,950, (Continued)

(51) Int. Cl.
*A61B 18/12*    (2006.01)
*A61B 18/14*    (2006.01)
(Continued)

(52) U.S. Cl.
CPC ...... *A61B 18/1206* (2013.01); *A61B 18/1402* (2013.01); *A61B 18/1477* (2013.01); *A61B 10/02* (2013.01); *A61B 2018/0072* (2013.01); *A61B 2018/00464* (2013.01); *A61B 2018/00565* (2013.01); *A61B 2018/00767* (2013.01); *A61B 2018/00827* (2013.01); *A61B 2018/1226* (2013.01); *A61B 2018/1266* (2013.01); *A61B 2018/143* (2013.01);
(Continued)

(58) Field of Classification Search
CPC . A61B 10/02; A61B 18/1206; A61B 18/1402; A61B 18/1477; A61B 2018/00464; A61B 2018/00565; A61B 2018/0072; A61B 2018/00767; A61B 2018/00827; A61B 2018/1226; A61B 2018/1266; A61B 2018/1425; A61B 2018/143; A61B 2018/1472; A61B 2218/002; A61N 1/0502; A61N 1/328
See application file for complete search history.

(56) References Cited

U.S. PATENT DOCUMENTS 7,416,550 B2    8/2008 Protsenko et al.
2003/0212394 A1*  11/2003 Pearson ............ A61B 18/1477
606/41
(Continued)

*Primary Examiner* — Michael F Peffley
*Assistant Examiner* — Khadijeh A Vahdat
(74) *Attorney, Agent, or Firm* — Shimokaji IP

(57) ABSTRACT

A method of altering adipose tissue includes creating an electrochemical reaction in the tissue, wherein the electrochemical reaction occurs in the presence of an electrolytic solution in the tissue.

26 Claims, 8 Drawing Sheets

Related U.S. Application Data which is a continuation of application No. 14/280,524, filed on May 16, 2014, now Pat. No. 9,877,770.

(60) Provisional application No. 61/824,299, filed on May 16, 2013, provisional application No. 62/462,937, filed on Feb. 24, 2017, provisional application No. 62/541,642, filed on Aug. 4, 2017.

(51) Int. Cl.
*A61B 18/00* (2006.01)
*A61B 10/02* (2006.01)
*A61N 1/32* (2006.01)
*A61N 1/05* (2006.01)

(52) U.S. Cl.
CPC ............... *A61B 2018/1425* (2013.01); *A61B 2018/1472* (2013.01); *A61B 2218/002* (2013.01); *A61N 1/0502* (2013.01); *A61N 1/328* (2013.01)

(56) References Cited

U.S. PATENT DOCUMENTS

2004/0236320 A1* 11/2004 Protsenko .............. A61B 18/14
 606/32
2010/0049192 A1* 2/2010 Holtz ................. A61N 1/36071
 606/41

* cited by examiner

| Voltage | pH (anode) | pH (cathode) | Distance of pH change (mm) |
|---|---|---|---|
| 3 | 6.5 | 7.5 | 2.5 |
| 4 | 5 | 8 | 3 |
| 5 | 4 | 9 | 3.5 |
| 6 | 3 | 10 | 4 |

METHOD AND APPARATUS TO ELECTROCHEMICALLY TREAT ADIPOSE TISSUE IN THE HUMAN BODY

CROSS-REFERENCE TO RELATED APPLICATIONS

This application is a continuation-in-part of U.S. patent application Ser. No. 15/841,213 filed Dec. 13, 2017, now U.S. Pat. No. 10,939,950, which is a continuation of U.S. patent application Ser. No. 14/280,524 filed May 16, 2014, now U.S. Pat. No. 9,877,770, both of which claim priority to U.S. provisional application No. 61/824,299 filed May 16, 2013, and all of which are incorporated herein by reference. This application also claims the benefit of U.S. provisional application nos. 62/462,937 filed Feb. 24, 2017 and 62/541,642 filed Aug. 4, 2017, both of which are incorporated herein by reference.

BACKGROUND OF THE INVENTION

The present invention generally relates to the treatment of adipose tissue and more, particularly to apparatus and methods of adipose tissue treatment by electrochemical changes.

In developed countries, there is an obesity epidemic, and apart from the obvious health related issues (e.g., cardiovascular disease, orthopedic injuries, and arthritis), another issue is disfigurement and change in body image. The removal of fat is a contemporary element of cosmetic surgery, which has progressed over decades from classic "resect and suture type approaches" to removing skin and fat as a composite tissue, to liposuction.

Liposuction has been developed in many centers throughout the globe, but Orange County, California leads in the development of liposuction technology, including the development of liposuction cannulas as well as specific techniques used. The development of so-called tumescent liposuction was pioneered in San Clemente, Calif., and involved the injection of saline solution mixed with a heavily diluted amount of lidocaine (a local anesthetic agent). This is injected in large volumes into the subcutaneous tissues in the targeted regions of interest. An anesthesia is locally achieved such that a liposuction cannula can be inserted through a small stab incision allowing the very simple removal of fat without the need for classic general anesthesia or sedation.

This approach is practiced now by numerous medical specialties including dermatologists who have no true surgical training. Because it can be performed as an office-based therapy, it has gained wide acceptance.

It should be noted, however, that the injection of tumescent solution into fat tissue is used to alter the mechanical property of fat by increasing tissue turgidity, and at the same time provide a local anesthetic. The tumescent solution in classic liposuction operations and related procedures does not participate actively in any chemical process, and does not need to contain any electrolytes as an active ingredient. Both lactated ringers solution and normal saline are used for tumescent liposuction, for example. It is often combined with small quantities of epinephrine which functions as a local vasoconstrictive agent to reduce bleeding.

Nevertheless, this still is a surgical procedure. Liposuction has evolved to include laser technologies, which have even used sophisticated technologies such as the thermal image guidance. Radiofrequency devices have also been used through needle based techniques to generate heat within fat stores to result in thermal denaturation and death of fat tissue. Along the same lines, noninvasive approaches have included using focused ultrasound waves, which results in the generation of heat deep into the skin with the same outcome as radiofrequency, but without the need to perforate the skin. It should be noted that current laser, RF and ultrasound technologies rely on thermal energy for the modification of fatty tissues.

Another approach to treating subcutaneous fat has involved combining suction and cooling from two opposed services that result in a freeze injury to fat and ultimately resorption of fat tissue. This so-called cryo-lipolysis does not result in the physical removal of fat tissue at the time of the procedure. The assumption is that the destroyed and emulsified fat molecules are resorbed by the body over time, and tissue remodeling occurs in the surgical treatment site resulting in a change in 3D contour.

Pharmacologic treatments have also been tried, and these have included the local injection of specific chemicals and other agents aimed at destroying fat tissue. Early chemicals tried included surfactants and detergents; however, complications related to their use resulted in abandonment of this class of molecules. More recently, the FDA has approved the use of deoxycholic acid, which is a naturally occurring acid found in the gallbladder, and is part of the physiology of fat digestion in the gut. Deoxycholic acid results in the lysis of large fat molecules, which results in the generation of smaller fatty acid chains. The small fatty acids can then readily cross the intestinal membranes and into the bloodstream. A synthetic formulation of deoxycholic acid, called Kybella®, has been recently approved by the FDA for injection into subcutaneous tissues whereby measurable changes in body contour and shapes have been achieved. This drug is used for very fine contour changes, such as in the sculpting of the contour below the chin.

Irreversible electroporation is another technology that has received some attention, and recently descriptions of this technology have been published on fat. Irreversible electroporation involves the application of very high-voltage electrical pulses to a tissue via needle electrodes. This exceptionally high electrical potential results in the disruption of cell membrane structure with alterations in permeability as well as trans cell membrane potential. This alters the physiology of the cell membrane, which then triggers cascades of cell death responses. Irreversible electroporation does not rely on electrochemical reactions in its mechanism of action. Furthermore, electroporation does not result in the emulsification of fat molecules themselves, but rather deaths of cells, likely through apoptosis.

As can be seen, there is a need for improved apparatus and methods for the treatment and/or shaping of adipose tissue.

SUMMARY OF THE INVENTION

In one aspect of the present invention, a method of altering adipose tissue, comprises creating an electrochemical reaction in the tissue; wherein the electrochemical reaction occurs in the presence of an electrolytic solution in the tissue.

In another aspect of the present invention, a method of altering adipose tissue, comprises using at least an anodic electrode and a cathodic electrode in the tissue to initiate an electrochemical reaction in the tissue; adding an electrolytic solution to the tissue.

In a further aspect of the present invention, a method of altering adipose tissue comprises mechanically disrupting the tissue; and electrochemically degrading the tissue.

In a still further aspect of the present invention, a method of altering adipose tissue comprises electrochemically generating sodium hydroxide, hydrogen gas, and either chlorine gas or oxygen gas at the tissue; and electrochemically forming acid/base species at the tissue.

In an additional aspect of the present invention, apparatus for altering adipose tissue comprises a non-linear electronic system configured to cause an electrochemical reaction in the tissue; wherein the electrochemical reaction occurs in the presence of an electrolytic solution.

In yet another aspect of the present invention, apparatus for altering adipose tissue comprises at least two electrodes configured to cause an electrochemical reaction in the tissue; wherein the electrochemical reaction occurs in the presence of an electrolytic solution; and a controller in communication with the electrodes and configured to: create an electrical potential across the electrodes; and cause an oxidation reaction in the tissue that is spatially distinct from a reduction reaction.

Herein, the terms "altering", "altered" or the like in the context of methods and apparatus of the present invention is intended to broadly mean, for example, affecting healthy and/or unhealthy tissue, and changing healthy and/or unhealthy tissue. As a further example, "altering", "altered" or the like may, for example, include treating, removing, degrading, damaging, absorbing, modifying, shaping, and/or sculpting tissue.

Various embodiments herein include a method of modifying a tissue, comprising providing an electrochemical interaction in a tissue, and modifying the tissue by exploiting the electrochemical interaction. In another embodiment, exploiting the electrochemical interaction comprises utilizing an electrochemical potentiostat to apply a specific electrical potential to an array of electrodes. In another embodiment, the electrodes are one or more needle electrodes inserted into the tissue. In another embodiment, exploiting the electrochemical interaction comprises potential-driven electrochemical modification of tissue (PDEMT). In another embodiment, the electrochemical interaction is optimized based on the identification and isolation of one or more discrete electrochemical reactions that cause shape change of the tissue. In another embodiment, the electrochemical interaction is optimized based on specific electrical dosimetry, electrode placement, and/or type of composition. In another embodiment, the tissue comprises a lipid. In another embodiment, the tissue comprises adipose tissue. In another embodiment, modifying the tissue is changing the physical shape of the tissue. In another embodiment, modifying the tissue comprises changing physical properties. In another embodiment, changing physical properties includes mechanical behavior-static and dynamic, electrical behavior, optical properties, and/or thermal properties. In another embodiment, modifying the tissue comprises changing biological behavior. In another embodiment, changing biological behavior includes shape change of the tissue, appearance of the tissue, and/or altering drug delivery properties of the tissue. In another embodiment, modification of the tissue is a part of an overall drug treatment regimen. In another embodiment, the modification of tissue is performed in tandem with one or more defined changes in mechanical state in tissue, temperature of tissue, pressure, compression, and/or atmospheric and ambient conditions. In another embodiment, exploiting the electrochemical interaction in the subject comprises use of a system comprising one or more electrodes and a control system to apply a precise electrical potential.

Other embodiments include a method of treating a disease and/or condition in a subject, comprising defining an electrochemical interaction in a constituent of a tissue in a subject, and treating the disease and/or condition by exploiting the electrochemical interaction in the subject. In another embodiment, exploiting the electrochemical interaction results in altering the constituent of living tissue. In another embodiment, the constituent is adipose tissue. In another embodiment, treating the disease and/or condition is the treatment of one or more biologic contaminants. In another embodiment, the one or more biologic contaminants include bacteria, fungi, molds, and/or viruses. In another embodiment, exploiting the electrochemical interaction in the subject comprises potential-driven electrochemical modification of tissue (PDEMT). In another embodiment, the subject is a human. In another embodiment, exploiting the electrochemical interaction in the subject further comprises placement of cathode and anode electrodes in an effective geometric arrangement. In another embodiment, modification of the tissue is as part of an overall drug treatment regimen. In another embodiment, the modification of tissue is performed in tandem with one or more defined changes in mechanical state in tissue, temperature of tissue, pressure, compression, and/or atmospheric and ambient conditions. In another embodiment, exploiting the electrochemical interaction in the subject comprises use of a system comprising one or more electrodes and a control system to apply a precise electrical potential.

Other embodiments include a system for exploiting an electrochemical interaction in a subject, comprising one or more electrodes, and a control system to apply a precise electrical potential. In another embodiment, the control system utilizes a potentiostatic control. In another embodiment, the control system utilizes a galvanostatic control. In another embodiment, the control system utilizes operation amplifiers. In another embodiment, the control system further comprises a feedback control. In another embodiment, the feedback control comprises monitoring tissue effect, change in mechanical properties, electrical properties, or optical properties, and total charge transfer. In another embodiment, the feedback control comprises a measure and control of current, potential, charge transfer, pH, concentration of species generated by the system, and/or evolution of gases. In another embodiment, the one or more electrodes comprises a working, reference, and auxiliary electrode, or a cathode electrode and an anode electrode. In another embodiment, the one or more electrodes have a static placement. In another embodiment, the one or more electrodes are within a flow through cell. In another embodiment, the one or more electrodes have a shape that is needle, flat plate, curved, clamshell, complex, screen, foam, solid-stiff, soft, pliant, moldable, conforming, and/or liquid. In another embodiment, the one or more electrodes are made from platinum, iridium, and/or graphite. In another embodiment, the one or more electrodes are coated with a plurality of oxidation catalysts. In another embodiment, the one or more electrodes comprise sequestered auxiliary electrodes in an isolated chamber connected by a salt bridge and/or luggin capillary. In another embodiment, the one or more electrodes are a reference electrode. In another embodiment, the one or more electrodes are composed of base metals and electro-plated. In another embodiment, the applied precise electrical potential is modulated. In another embodiment, the applied precise electrical potential is modulated by pulsed, complex or simple waveform, and/or on and off cycles. In another embodiment, the control system is adapted for use in conjunction with open surgery, endoscopic delivery, percutaneous, transmucosal, in an air environment, in an aqueous environment, image guided therapies to target specific tissues and/or targets, biopsy, and/or tissue sampling. In another embodiment, the control system is used in tandem with one or more of the following: agents that activate a pro-genic drug, user created changes in tissue composition, injectable drugs, agents that produce cross-linking of proteins, agents that alter pH, activate a catalyst for tissue effects, osmotically active agents, saline solutions, buffers, reactive oxygen scavengers, and chemicals that alter electrochemistry of the system. In another embodiment, the system further comprises a plurality of set of electrodes. In another embodiment, the plurality of set of electrodes are used simultaneously or at different times. In another embodiment, the plurality of set of electrodes are used at the same location or spaced apart. In another embodiment, the plurality of set of electrodes are in a multiplexing arrangement of the specific chemical reaction desired. In another embodiment, the system further comprises using an electrochemistry reaction to generate an active polymerization catalyst. In another embodiment, the system further comprises polymerization of polyanaline, polypyrrole, and/or polythiophene.

Various embodiments include a method of shaping adipose tissue in a patient, comprising providing a potential-driven electrochemical modification of adipose tissue (PDEMT) device, and using the device to shape adipose tissue in the patient. In another embodiment, adipose tissue is shaped by water electrolysis that results in protonation of fixed negative charges. In another embodiment, the method further comprises increasing tissue viability by minimizing pH gradients and/or ROS generation. In another embodiment, the device incorporates bipotentiostat and/or polypotentiostat technology.

Other embodiments include a method of treating an adipose tissue malformation condition in a patient, comprising providing a potential-driven electrochemical modification of tissue (PDEMT) device, and treating the patient by using the device to treat adipose tissue. In another embodiment, the device incorporates bipotentiostat and/or polypotentiostat technology.

Other embodiments include an apparatus, comprising a potential-driven electrochemical modification of tissue (PDEMT) device adapted for shaping adipose tissue in a patient. In another embodiment, the device incorporates bipotentiostat and/or polypotentiostat technology.

These and other features, aspects and advantages of the present invention will become better understood with reference to the following drawings, description and claims.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
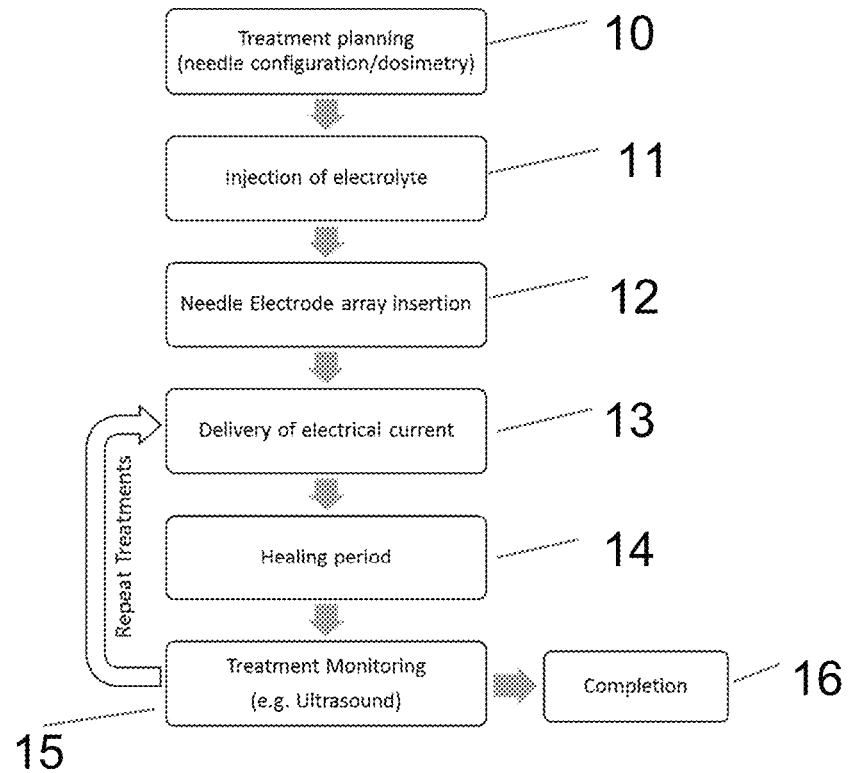
FIG. 1 is a flow chart depicting a method of electrochemical lysis of fat (ELF) in accordance with an embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

All references cited herein are incorporated by reference in their entirety as though fully set forth herein. Unless defined otherwise, technical and scientific terms used herein have the same meaning as commonly understood by one of ordinary skill in the art to which this invention belongs. Singleton et al., Dictionary of Microbiology and Molecular Biology 4th ed., J. Wiley & Sons (New York, N.Y. 2012); March, Advanced Organic Chemistry Reactions, Mechanisms and Structure 5th ed., J. Wiley & Sons (New York, N.Y. 2001); and Sambrook and Russel, Molecular Cloning: A Laboratory Manual 4th ed., Cold Spring Harbor Laboratory Press (Cold Spring Harbor, N.Y. 2012) provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the abbreviation "PDEMT" refers to potential driven electrochemical modification of tissue.

As used herein, the abbreviation of "ELF" means electrochemical lysis of fat which can incorporate one or more aspects of PDMET and/or EMR.

Broadly, the present invention provides electrochemical lysis of adipose tissue and other related tissues with introduction of electrolytes into tissues for the purpose of cosmetic or plastic surgery or for other medical treatments (e.g., adipose tumors). The present invention can be used for reduction treatments of submental fat and cellulite.

Generally, in this invention, electrolytic solution is injected into the subcutaneous fatty tissues that need to be treated, and needle electrodes are inserted through the skin into fat tissues. The needles are connected to an electrical power source—as simple as a battery—which triggers chemical reactions around the needles that result in the production of hydrogen gas (at the cathode) and oxygen gas (at the anode). These reactions also raise and lower the pH in vicinity of the respective electrodes.

By employing a conventional potentiostat—an electrical circuit based on an inexpensive operational amplifier—to control the electric fields, it is possible to monitor and control precisely the quantities of acids and bases produced. By enabling control over the applied voltages, the potentiostat allows selection of specific electrochemical reactions with tight spatial resolution. Both acids and bases can hydrolyze or otherwise chemically modify fat molecules. Later on, hydrolyzed fat is absorbed by the body, and the region treated assumes a better appearance. This invention can be useful in removal or sculpting of localized fatty tissues that cannot be easily removed using conventional liposuction.

The present invention can be implemented for the treatment, shaping, and/or removal of adipose tissue. For electrochemical reactions to occur, the milieu in which the reactive species reside within tissues must conduct electrical current. Fat is a dielectric and insulator, and electrical current is not readily transmitted through it, and thus establishing an adequate electrical potential to drive electrochemical reactions in fatty tissue is a challenge, and resistive heating may occur which can lead to uncontrolled thermal injury.

To overcome this challenge, this invention can incorporate the injection of an electrolyte solution—most commonly normal saline—into the subcutaneous tissue. In embodiments, the electrolytic solution may contain one or more amphiphilic compounds. The injection may occur before or during the application of the electrical potential. This can be combined with a local anesthetic as well to reduce or eliminate pain associated with electric current. The injection of saline solution into fat tissues results in a change in the electrical impedance of this tissue and allows the flow of charge from anode to cathode. With the establishment of the appropriate electrical potential, water then undergoes electrolysis. Reactive species are generated, the most important being hydronium (protons) and hydroxyl ions.

FIG. 1 is a flow chart of an exemplary method of electrochemical lysis of fat tissue (ELF) according to the present invention. In an embodiment, a step 10 may include treatment planning 10, a step 11 may include injecting an electrolyte into the tissue, a step 12 may include inserting electrode needles into the tissue, a step 13 may include applying an electrical potential or potential difference to the electrodes, a step 14 may include allowing the tissue to alter, a step 15 may include monitoring the altering process which may occur at any point during the process, and a step 16 may include the completion of altering the tissue.

Figure 2:
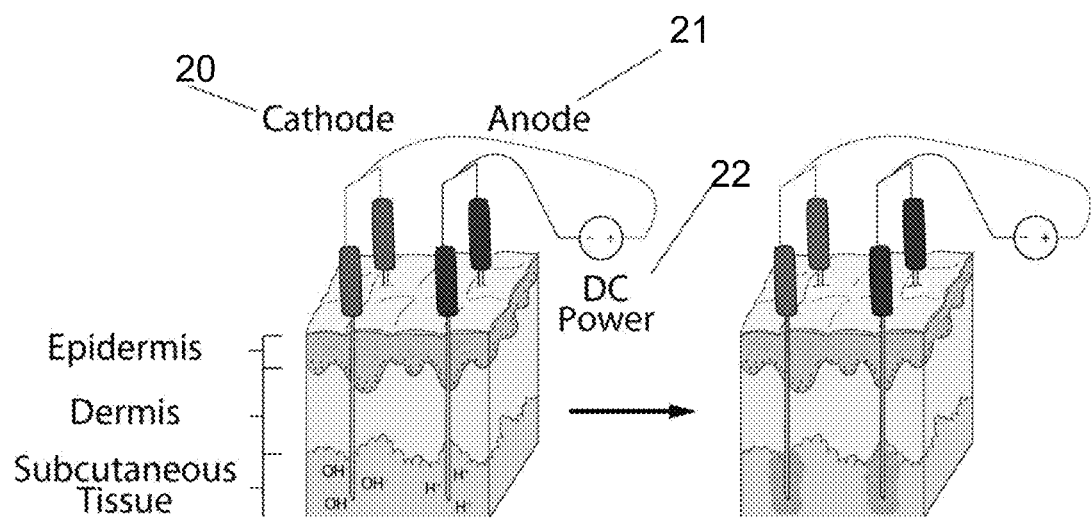
FIG. 2 is a schematic diagram of apparatus for ELF in accordance with an embodiment of the present invention.

FIG. 2 is a schematic diagram of exemplary apparatus that may be employed in a system for carrying out a method of ELF according to the present invention. In an embodiment, two pairs of cathodes (20) and anodes (21) are configured in an array and electrically driven by a DC power supply 22. According to this exemplary embodiment, the electrode needles 20, 21 can be insulated in and near their mid-shaft portions to protect the epidermis and dermis layers. The non-insulated distal or conductive ends of the electrodes can extend into the subcutaneous tissue to enable electrochemical reactions therein. These reactions can drive pH change in the vicinity of the electrodes to create low-grade disruption, degradation, and/or damage to the subcutaneous tissue.

Figure 3:
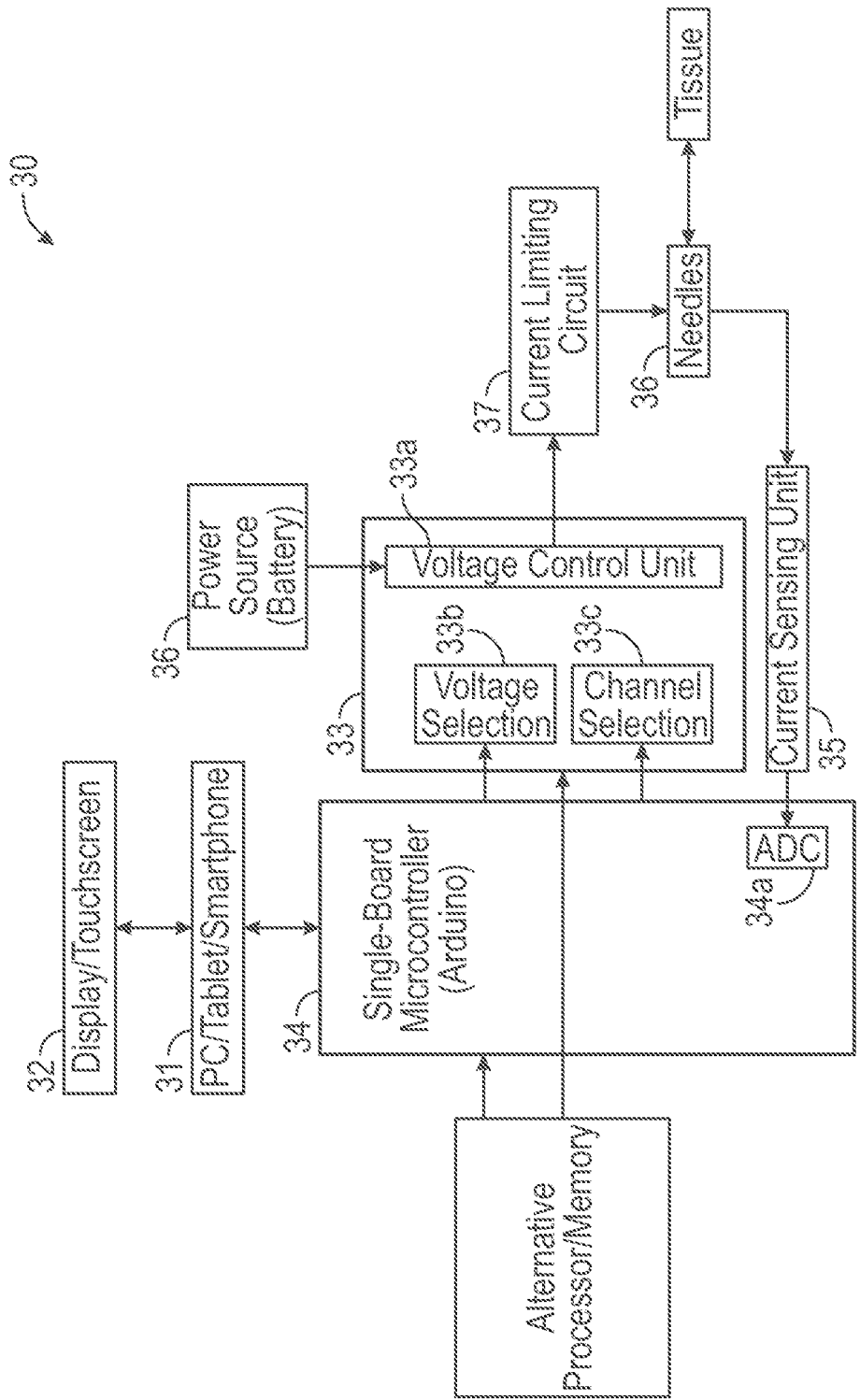
FIG. 3 is a block diagram of a system for ELF in accordance with an embodiment of the present invention.

FIG. 3 is a block diagram of an exemplary system for ELF in accordance with the present invention. According to this exemplary embodiment, a system 30 may include a computer 31 with a display 32, which can communicate with a controller 34. In turn, the controller 34 may control a circuit 33 that can include a voltage control unit 33a, a voltage selection unit 33b, and a channel selection unit 33c. For example, the voltage selection unit 33b may enable a user to select a voltage to be applied to a current limiting circuit 37 described below, while the channel selection unit 33c may enable the user to select one or more electrode pairs to be activated in the tissue.

The system 30 may further include a power source 36 may supply power, via the voltage control unit 33a, to a current limiting circuit 37. In turn, the current limiting circuit 37 can apply a potential across cathode and anode needles 36. A current sensing unit or circuit 35 can monitor the current across the needles and provide feedback information, via an analog to digital converter 34a, to the controller 34.

Though the foregoing example is described in the context of wired circuitry, the present invention contemplates that the same can be implemented in software.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable media having computer readable program code embodied thereon.

Any combination of one or more computer readable storage media may be utilized. A computer readable storage medium is an electronic, magnetic, optical, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium is any tangible medium that can store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable storage medium that can direct a computer, other programmable data processing apparatus, or other devices to function in a particular manner, such that the instructions stored in the computer readable storage medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Implementation of the method, apparatus and system of the present invention can have numerous effects. In adipose tissue, this can result in the breakdown of the fat cell membrane, as well as hydrolysis of the fat molecules themselves. High concentrations of both acid and base can have a major effect on adipose tissue. The tissue effect can be spatially limited to the immediate vicinity of the electrodes because the interstitial fluids of the body are a heavily buffered system. The other factors governing the spatial limits of the tissue effects are the electric field gradient and the chemical gradient. Notably, as gas ($H_2$ and $O_2$) is evolved, this can form a natural and obvious contrast media which can be readily detected using ultrasound or similar imaging technologies. The combination of this electrochemical treatment with ultrasound imaging provides a means to monitor and feedback control the tissue effect. Likewise, dosimetry may be established using electrical feedback as well to monitor total charge delivery which directly relates to the amount of water electrolyzed.

The present invention can reduce or eliminate subcutaneous fatty tissues by first diffusely injecting an electrolyte solution (e.g., saline solution, lactated Ringer's) into the target subcutaneous fatty layer and then inserting a pair, array, or multiple needle electrodes into the target fatty tissue. A low voltage with floating, constant or pulsed current can be delivered to the electrodes from a DC power source (such as a battery) or a potentiostat. With the electric field turned on, the electrolysis can be triggered and can generate acid and base molecules. Electrochemically produced acidic and basic species can then cause breakdown of fat molecules as well as adipose cells. The process can be feedback controlled via a number of mechanisms including monitoring of charge transfer (current) and/or imaging. Imaging is important, as a byproduct of water electrolysis is molecular oxygen and hydrogen. These gases can create significant acoustic impedance changes in tissue. This can provide good contrast for ultrasonic imaging which can be used to directly monitor the spatial extent of tissue change.

In the present invention, the change to fatty tissues can be both mechanical and electrochemical. The use of numerous needle arrays can create mechanical disruption followed by the electrochemical disruption and/or degradation from the generation of acid and base, all in a highly localized manner.

In the present invention, electrochemistry of biological tissues at low voltage (i.e., applied potentials of roughly ±2 V vs. the normal hydrogen electrode) involves mainly water electrolysis at the tissue/solution interface. Electrolysis of saline solutions (or tissue fluids) generates sodium hydroxide and hydrogen gas at the negative electrode and chlorine gas, oxygen gas, or both at the positive electrode. Species generated do depend upon the potential as well as the electrode composition and electrical circuit design.

The fat breakdown process involving electrochemical lysis of fat (ELF) according to the present invention can be attributed to the formation of acid/base species at the electrodes. For example, saponification or "soap production" involves hydrolysis of fat (triglycerides) with sodium hydroxide, which is generated at the negative electrode in this invention. The chlorine gas produced at the positive electrode within a saline solution rapidly converts to hypochlorous acid in aqueous solution. Sodium hypochlorite, commonly known as bleach, is known to degrade fatty acids. In addition, sodium hypochlorite is highly reactive towards proteins and other biological molecules.

The ELF process of the present invention has unique advantages over the use of simple chemical methods, as the electrochemical treatment can be highly localized to needle tips by using needle electrodes. Use of microneedle arrays may provide efficient treatments since the microneedles can create mechanical disruption of fatty tissues followed by electrochemical disruption and/or degradation. In addition, the dosage scheme in ELF of the present invention can be controlled by the amount of electrolyte injection, needle configuration, voltage, and the total current delivered. Availability of multiple parameter control would then allow physicians to better fine-tune the treatments for best outcome. The ELF process of the present invention is not drug delivery and relies upon a medical device to alter the physiological milieu surrounding fat cells (adipocytes).

Furthermore, the present invention can be used in combination with a biological fat emulsifier (e.g., deoxycholic acids) as a combination therapy. Fat emulsifiers can be delivered into tissue as a mix in the electrolytic solution or after the electrochemical treatments, which may enhance the efficiency of the emulsifier.

As disclosed herein, ELF can include one or more aspects of PDEMT. Accordingly, the present invention involves the role of electrical potential rather than voltage differences, as one can isolate and identify the precise electrochemical reactions that cause events such as shape change or tissue injury. Instead of applying a large voltage difference between two electrodes, the present invention can utilize an electrochemical potentiostat to apply a specific electrical potential to an array of electrodes where discrete electrochemical reactions can be isolated. Hence, reactions that favor shape change can be selected over those that cause tissue injury. The present invention can capitalize on the innate structure of adipose tissue as a lipid, where part of the shape-change process is related to the interplay between charged macromolecular matrix components (proteoglycans), free ions, water, and electrochemical reactions at the interface between tissue and electrode.

In one embodiment, the present invention provides a method of shaping adipose tissue by using a minimally invasive, needle based approach. As further described herein, in one embodiment, a potentiostat is incorporated to control potential rather than simply applying a voltage difference. This can overcome a significant limitation in that specific chemical reactions can be used for therapy and while others are rejected.

In one embodiment, the incorporation of potentiostat technology is used to select specific electrochemical potentials to isolate specific chemical reactions. In another embodiment, the present invention is used to choose between one anodic and/or cathodic half-reaction thereby potentially enhancing/diminishing undesirable outcomes. In another embodiment, the incorporation of a potentiostat is used for multiple tissue electrodes. In another embodiment, the present invention is used to contain and/or localize undesirable half-reactions to a site distal to tissue of interest (even with the use of a sacrificial electrolyte outside the tissue).

In one embodiment, the technology allows for the use of chemically modified electrodes to further select specific electrochemical reactions to optimize shape and mechanical properties change/minimize tissue damage. The potentiostat can operate in modes where a constant voltage is applied, a constant current is applied, operating in galvanostatic mode, or a pulsed, alternating, or ramped application of voltage or current is used to optimize the concentrations of electrochemically generated species that affect tissue shape change. In another embodiment, the amount of electric charge transferred through each electrode of the potential-driven electrochemical modification of tissue (PDEMT) system is monitored and controlled by switching on/off individual electrodes and controlling applied voltage/current.

In other embodiments, the present invention provides a method of shaping adipose tissue in a patient, comprising providing a potential-driven electrochemical modification of tissue (PDEMT) device, and using the PDEMT device to shape adipose tissue in the patient. In another embodiment, adipose tissue is shaped by water hydrolysis that results in protonation of fixed negative charges. In another embodiment, the invention further comprises increasing tissue viability by minimizing pH gradients and/or ROS generation. In another embodiment, the device incorporates bipotentiostat and/or polypotentiostat technology.

Other embodiments include a method of treating an adipose tissue condition in a patient, comprising providing a potential-driven electrochemical modification of tissue (PDEMT) device, and treating the patient by using the PDEMT device to shape adipose tissue. In another embodiment, the device incorporates bipotentiostat and/or polypotentiostat technology.

Other embodiments include an apparatus, comprising a potential-driven electrochemical modification of tissue (PDEMT) device adapted for shaping adipose tissue in a patient. In another embodiment, the device incorporates bipotentiostat and/or polypotentiostat technology.

In another embodiment, general surgical or medical device technology may be used to deliver electrical charge or energy to adipose tissue to create in situ electrochemical reactions. In another embodiment, the present invention provides use of electrochemistry to control and generate specific user defined chemical reactions in regions defined by electrode placement and geometry. In another embodiment, the invention provides species (agent) selectivity and/or spatial selectivity. As readily apparent to one of skill in the art, a variety of treatments and applications to adipose tissue that require control and optimization may be used in conjunction with various embodiments herein. For example, interactions created can result in the modification of a target tissue for medical therapeutic effects including, change in physical properties (such as mechanical behavior—static and dynamic, electrical behavior, optical properties, or thermal properties), or changes in biologic behavior (such as cell injury, cell death, cancer treatment, cell proliferation, shape change of tissue, appearance of tissue, alter drug delivery properties of tissue). Or, for example, it may be performed in tandem with user imposed or defined changes in mechanical state in tissue (user defined stress-strain), temperature of tissue (heated or cooled), pressure/compression (internal stress), or atmospheric and ambient conditions.

As further described herein, in one embodiment, the present invention provides for a system that controls the process of current delivery or potential application. In another embodiment, the system has several electrodes including working, reference, and auxiliary, or cathode and anode. These electrodes can be placed into tissue in varying geometric arrangements. In another embodiment, there may be more than one of each of these types of electrodes within a therapeutic system. As apparent to one of skill in the art, any number of electrode shapes and materials are readily available and may be used in conjunction with various embodiments herein. For example, the electrode can be static or within a flow through cell, or in the shape of needles, flat plates, complex shapes (such as curves, or clamshell), screens, foams, solid-stiff, soft, pliant, moldable, conforming, or liquid (such as mercury, and other alloys). Or, for example, electrodes could be made of platinum, iridium, graphite, coated with oxidation catalysts, sequestered auxiliary electrodes in an isolated chamber connected by a salt bridge or Luggin capillary, reference electrode, or composed of base metals and electro-plated. Similarly, the electrodes may be placed in any number of useful geometric arrangements. For example, in one embodiment, cathode and anode electrodes may be placed within the tissue in either close proximity or at a distance from one another. Or, in another embodiment, an array of electrodes may be fashioned to cover a large or unique region of interest. In another embodiment, the reference electrode may not interact directly with tissue of interest (e.g., separated by a Luggin capillary or salt bridge). In another embodiment, the auxiliary electrode may not interact directly with tissue of interest (e.g., separated by a Luggin capillary or salt bridge). In another embodiment, the electrical current, charge transfer, and/or potential are modulated. In another embodiment, modulation includes pulsed, complex or simple waveform, and/or on and off cycles. In accordance with various embodiments herein, more than one system or set of electrodes can be used, which can include simultaneously or at different times, or at the same location or spaced apart with variable or constant distances, or multiplexing of the specific chemical reaction desired.

As further disclosed herein, the system that controls the process of current delivery or potential application may also include one or more control system instrumentations. As readily apparent to one of skill in the art, there are a variety of available devices and systems that may be used to provide control instrumentation, as well as any number of elements that may be desired to be monitored and controlled in accordance with various embodiments herein. In one embodiment, the control system instrumentation is a potentiostatic control. In another embodiment, potentiostat includes bipotentiostats. In another embodiment, the potential is specified by the user. In another embodiment, the control system is a galvanostatic control, where the user can specify certain amounts of current, and potential will be set to establish that current. In another embodiment, simple operation amplifiers can function to accomplish the task of a potentiostatic and/or galvanostatic control. In another embodiment, the system further includes a feedback control. This may include control of tissue effect, where biophysical change can be monitored and information used to control current and/or potential. Or, for example feedback control may include monitored variables that include mechanical properties, electrical properties, and optical properties. In another embodiment, total charge transfer is also monitored. In accordance with various embodiments herein, control system instrumentation may be used to measure and/or control one or more of the following: current, potential, charge transfer, pH, concentration of various species generated by the device, and/or the evolution of gases.

In another embodiment, the device is designed for use in air and in aqueous environments, combined with image guided therapies to target specific tissues/targets, or perform simultaneous functions such as biopsy and tissue sampling. In accordance with various embodiments herein, the device may be used in tandem with one or more agents that activate a pro-genic drug (e.g., tumorcidal). This may include, for example, reactive oxygen species, generate in situ species, or the circumstance where the drug is activated only in vicinity of appropriate/extreme user defined electrical potential. Defined electrical potential may include, for example, creating spatial selectivity based electric field, or isolate deleterious or desired reaction to what is defined by electrode placement geometry. In accordance with various embodiments herein, the device may be used in tandem with user created changes in tissue composition, injectable drugs, agents that produce cross-linking of proteins, agents that alter pH, or activate a catalyst for tissue effects including glue, tumorcidal, or mechanical property change, etc. Similarly, the device may be used in tandem with one or more of the following: osmotically active agents, saline solutions (hyper and hypotonic), buffers, reactive oxygen scavengers, and other chemicals that change or alter electrochemistry of the system.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overview

In one embodiment, potential driven electrochemical modification of tissue (PDEMT) is a technology that can be used to create discrete electrochemical reactions in tissue. In one embodiment, a potentiostat is employed to select and control the specific electrochemical reactions that occur at an electrode-tissue interface. A potentiostat is the electronic hardware based upon operational amplifiers or other non-linear electrical circuits, and is required to control a three electrode cell and run most electroanalytical experiments. A bipotentiostat and polypotentiostat are potentiostats capable of controlling two working electrodes and more than two working electrodes, respectively. PDEMT implicitly is a new treatment modality that relies upon control of redox chemistry. Redox reactions, or oxidation-reduction reactions, have a number of similarities to acid-base reactions. Like acid-base reactions, redox reactions are a matched set, that is, there cannot be an oxidation reaction without a reduction reaction happening simultaneously. The oxidation alone and the reduction alone are each called a half-reaction, because two half-reactions always occur together to form a whole reaction. When writing half-reactions, the gained or lost electrons are typically included explicitly in order that the half-reaction be balanced with respect to electric charge. A potentiostat allows the separation of the two half-reactions spatially which is important, as in living tissues the major redox reaction that occurs with PDEMT is the electrolysis of water. Complex species may be generated with hydrolysis and PDEMT permits a means to isolate desirable reactions and reduce or eliminate those which are deleterious.

Example 2

Incorporation of Potentiostat Technology

The incorporation of potentiostat technology can be important in implementation of this technology as one may a) select specific electrochemical potentials to isolate specific chemical reactions; b) choose between one anodic and/or cathodic half-reaction thereby potentially enhancing/diminishing undesirable outcomes; c) use multiple tissue electrodes; and d) potential to contain/localize undesirable half-reactions to a site distal to the tissue of interest (even with the use of a sacrificial electrolyte outside the body, tissue, or organ). The technology additionally allows for the use of chemically modified electrodes to further select specific electrochemical reactions to optimize shape and mechanical properties change/minimize tissue damage. The potentiostat can operate in modes where a constant voltage is applied, a constant current is applied (operating in galvanostatic mode), or a pulsed, alternating, or ramped application of voltage or current is used to optimize the concentrations of electrochemically generated species that affect tissue shape change. In addition, the amount of electric charge transferred through each electrode of the bi-/multi-potentiostat PDEMT system can be monitored and controlled by switching on/off individual electrodes and controlling applied voltage/current.

Example 3

Experimental Set Up

Figure 4:
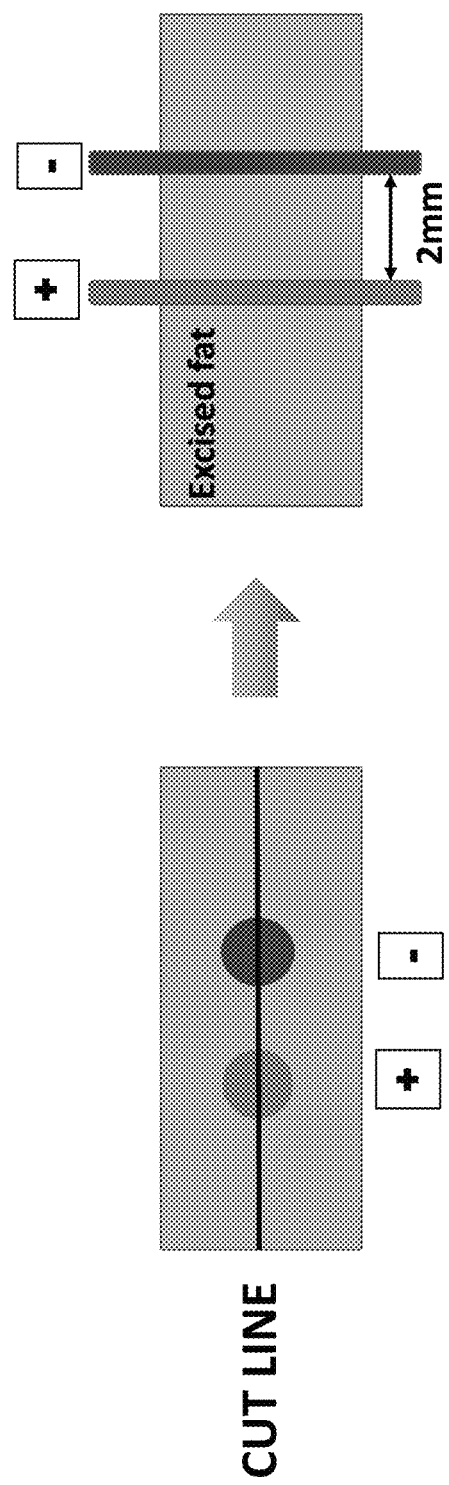
FIG. 4 is a schematic diagram of an experimental set up for testing ELF in accordance with an embodiment of the present invention.

FIG. 4 depicts an experimental set up for testing ELF, and mapping pH changes, according to the present invention. A cathode and an anode were placed 2*mm* apart in ex vivo porcine tissue. After ELF treatment, the tissue was sliced along the horizontal plane to dissect through the middle of the electrodes.

Experiments

Porcine skin was sectioned into 1.5 in×1.5 in×1 in samples. The samples were maintained in phosphate buffered saline (PBS) at 4° C. Before the application of ELF, the samples were removed from PBS and allowed to dry in air for 10 minutes. The samples were subjected to ELF using dosimetry parameters of 5 volts and 5 minutes, with both injection of saline locally within the ELF needle electrode injection site, and no injection of saline. Imaging was performed using a dermatologic ultrasound system (Esaote MyLab50, Esaote North America, Indianapolis, Ind.). Ultrasound imaging was performed with specimens immediately after electrochemical therapy (ECT) treatment at one minute intervals until the conclusion of ECT.

Platinum needle electrodes (0.3 mm diameter, Grass Technologies, West Warwick, R.I.) were chosen for their high standard potential and minimal risk of electrode oxidation. The electrodes were connected to a DC power supply (Model E3646A, Agilent Technologies, Santa Clara, Calif.), where 5 volts were applied to the experimental samples for 5-15 minutes. The electrodes were placed into the fat and no voltage was applied to control groups. Voltage was controlled and current was monitored using a MATLAB program and PC workstation. A needle array (3×4 needle array, 2 mm spacing between electrodes) was evaluated. When voltage was terminated, the needle electrode array was removed. The specimens were imaged with ultrasound before, during and after ELF treatment.

A clinical high frequency dermatologic ultrasonography system (Esaote North America, Indianapolis, Ind.) was used to image the tissue. The device features a 10 MHz transducer frequency and was placed directly on top of the skin, perpendicular to the needle electrode array placement.

Results

Figure 5A:
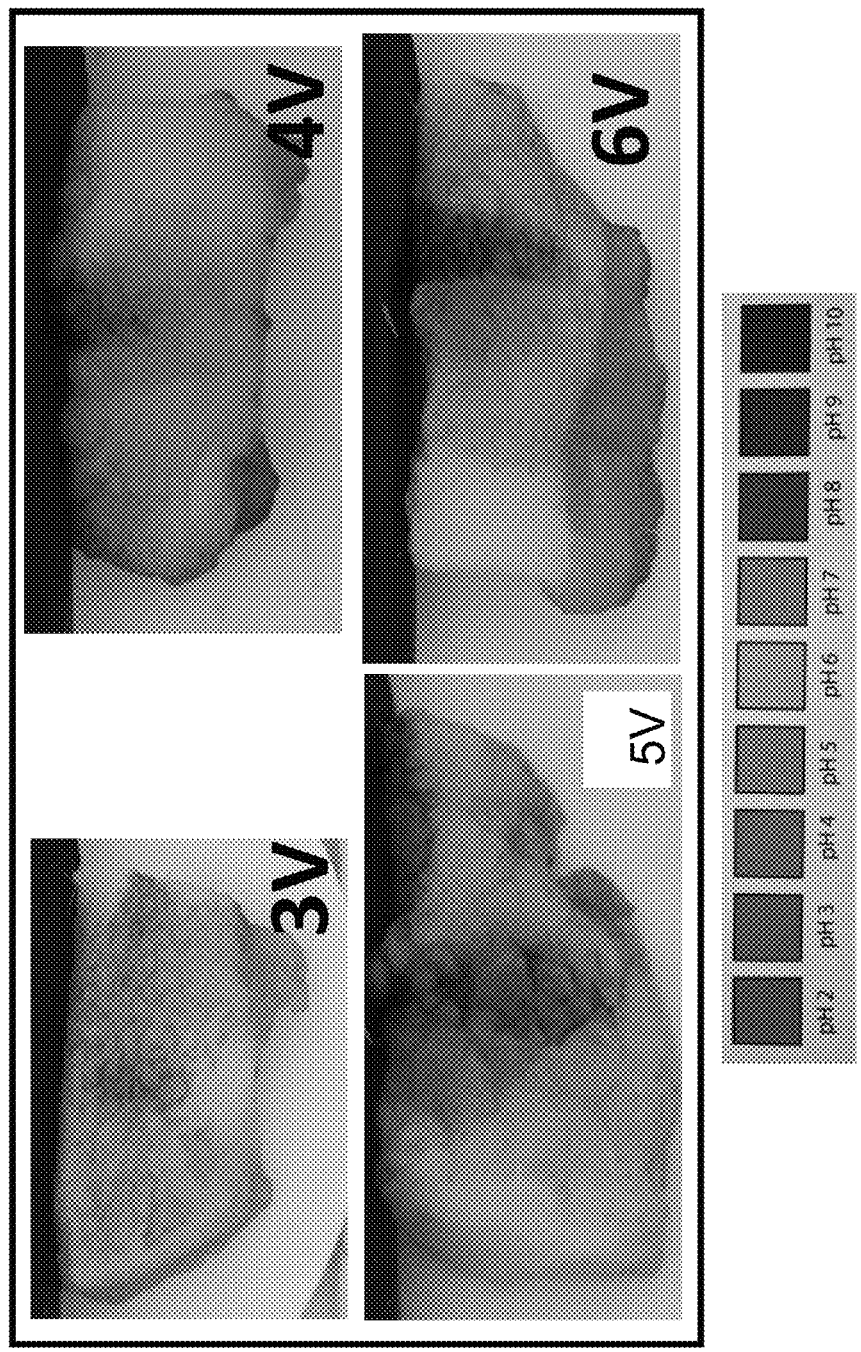
FIG. 5A are pictures of ex vivo porcine tissue after ELF in accordance with an embodiment of the present invention.

FIG. 5A is an image panel of dissected porcine fat after electrochemical lysis has been performed. pH indicator dye was applied after dissection along the plane of the needle pairs. The greenish color of background tissue—far from the center matches the color of pH 7. In the cathode, there is reduction of chemicals thus increasing the pH. In the anode, there is oxidation of chemicals and thus showing lower pH. A universal indicator pH test chart is shown as a reference.

Figures 5B, 5C:
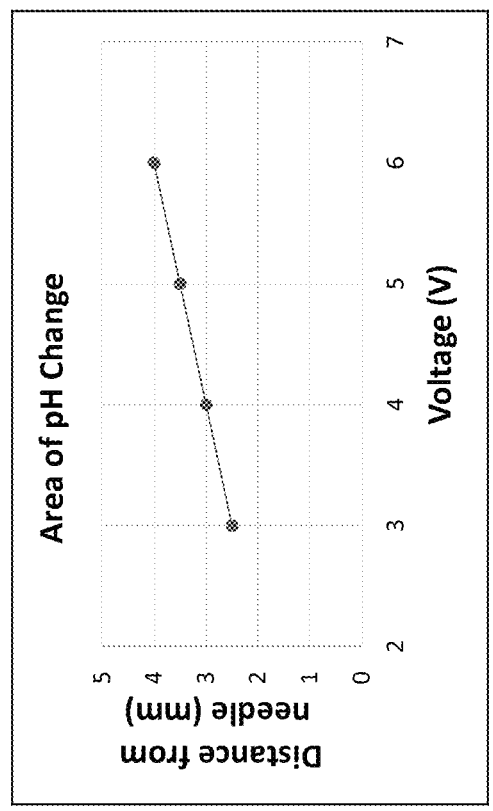
FIG. 5B is a table of the ELF characteristics shown in FIG. 5A.
FIG. 5C is a graph of distance from needle versus voltage for the results shown in FIG. 5A.

FIG. 5B is a table of pH changes around the electrode as compared to the color chart. The table shows the largest pH observed around each electrode for a given constant voltage applied. The distance from the electrodes indicates where there was significant pH change in the tissue.

FIG. 5C is a graph of the distance from the electrodes where significant pH change occurred. Increasing voltage showed larger areas around the electrodes of pH change.

Figure 5D:
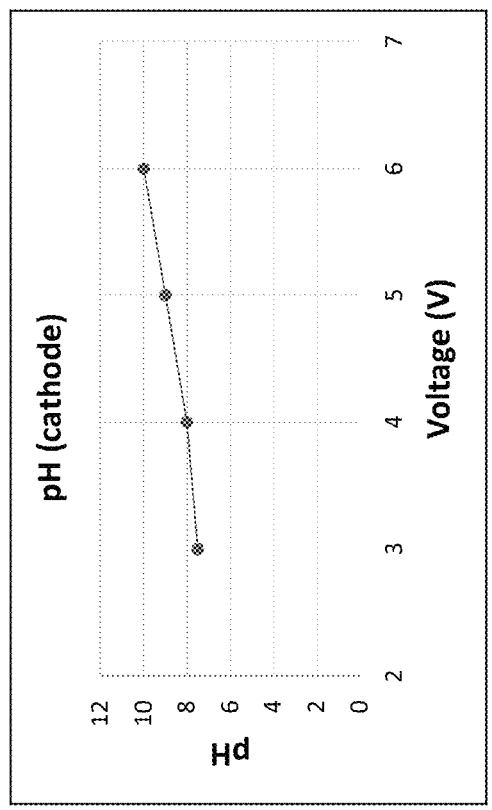
FIG. 5D is a graph of pH (cathode) versus voltage for the results shown in FIG. 5A.
Figure 5E:
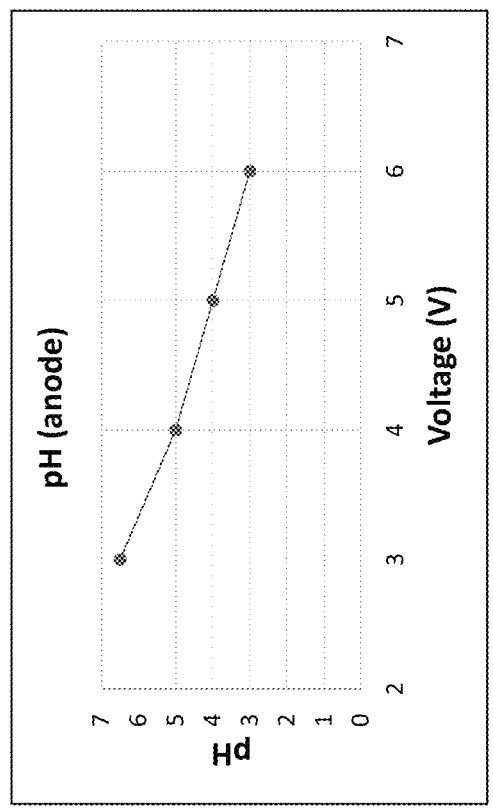
FIG. 5E is a graph of pH (anode) versus voltage for the results shown in FIG. 5A.

FIGS. 5D and 5E respectively show pH changes around the cathode (negative electrode) and the anode (positive electrode) according to the pH color scale above. For the cathode, increasing voltage results in higher pH due to increased reduction of chemical. For the anode, increasing voltage results in lower pH due to increased oxidation of chemicals.

Figure 6:
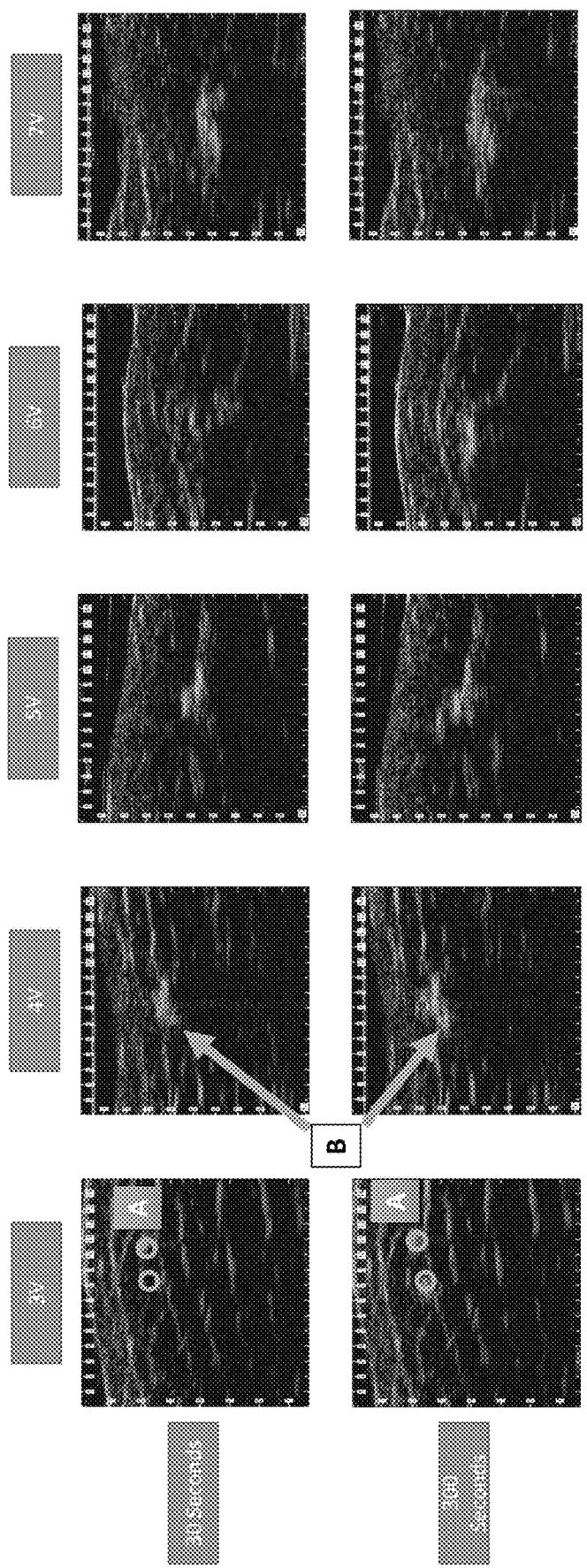
FIG. 6 are ultrasound images of post-ELF treatment of ex vivo porcine tissue in accordance with an embodiment of the present invention.

FIG. 6 are ultrasound images of ex vivo porcine after ELF. At "A", two gray circles denote the approximate location of electrodes. At 3V there was no significant structural damages to the fat tissue as evidenced by periodically ordered sonographic structures from adipose cell interfaces. At "B", as the voltage is increased, the area between electrode became denser (at 4V). The dark area below the electrodes are sonographic shadows created by the dense tissue formed. With increasing voltage and time, the disruption of periodic structures became larger and denser. Note that the images can be distorted due to irregular boundary conditions, which seem to increase with increasing voltage and time.

CONCLUSIONS

Potential-driven electrochemical modification of tissue (PDEMT) can be used to alter the mechanical structure of adipose tissue. Using this technology, tissue can be stretched, shortened, bended, curved, strengthened, and weakened. Also, this technology can be used to focally create electrochemical changes locally in tissue as well. This technology creates electrochemical changes in tissue using a unique means to control the delivery of electrical energy and create specific user-defined electrochemical reactions in localized or diffuse regions in the tissue. The technology allows separation of anodic and cathodic redox chemistry reactions to distinct sites that may be adjacent to one another or separated spatially. This invention relies upon principles of electrochemistry to alter the complex chemical milieu in adipose tissue to achieve structural changes and macromolecular alters in the matrix.

Conventional surgery requires skin incisions, almost always general anesthesia, longer operative times and recovery, and additional loss of time from work. The present inventive techniques are well suited to alter the shape of native tissue, and minimally invasive needle-based techniques could be used for in the office under local or regional anesthesia.

ELF does not rely upon resistive heat generation, but rather exploits the molecular properties of the adipose tissue to alter its mechanical state in response to changes in the electrical and chemical milieu that interacts with its charged tissue matrix. ELF is an ultra-low cost, needle-based therapy that can be implemented using only local anesthetics in most applications, and is suitable for office-based procedures. It represents a paradigm shift in that only electrochemical interactions in tissue are exploited to alter the material properties of fatty tissues, leading to a safe approach to tissue reshaping. ELF represents a significant move away from "cut and suture" surgery toward in situ techniques that exploit precisely controlled chemical reactions to restructure tissue at the molecular level. In addition to the simple needle electrodes and power supplies (e.g., disposable batteries) used for ELF may also include an operational amplifier-based circuit for the application of a controlled potential. Thus, ELF is low cost and amenable to single-use applications (disposable components); indeed, because the potentiostat can be computer controlled, algorithms for the optimal ELF conditions can be pre-programmed into the clinical device to reduce the reliance of good surgical outcome on the individual surgeon's technical skill, much in the model of LASIK cornea reshaping (albeit at a minute fraction of the cost).

Because ELF is, at the molecular level, a consequence of electrode-driven chemical reactions, it builds upon a knowledge base derived from nearly a century of chemistry research in electrochemical processes. That basic research has played key roles in developing industrial technologies ranging from the lithium-ion battery to personal glucose monitors. It is notable that both major professional electrochemical societies—the International Society of Electrochemistry (ISE) and the Electrochemical Society (ECS)—have formal divisions in bioelectrochemistry, yet those divisions focus largely on the electrochemical properties of individual biomolecules (proteins and DNA), or on the development of electrochemical assays for drug metabolites and other molecular markers. The application of modern electroanalytical methods to investigate the effects of electrochemical reactions on macroscopic tissue is virtually unheard of, and offers an innovative model at the interface of basic chemistry, biomedical engineering, and medicine. ELF has the potential to revolutionize the reshaping and/or treatment of adipose tissue.

The inventors have studied the molecular basis of ELF: most notably, they have established that ELF depends on specific electrochemical reactions at the tissue/solution interface, and examined the role of electrical potential. With the molecular mechanism(s) of ELF fully characterized, the application of electric fields using ELF may be tailored to select the specific reactions that create shape change while minimizing (or even eliminating) the reactions that cause tissue damage and cell morbidity.

Understanding the underlying molecular mechanism(s) of ELF is important to commercializing the reshaping process. Although several possible mechanisms may play a role (e.g., non-Faradaic protein and/or ion migration through the tissue caused by applied voltage gradients), the inventors' work supports that the dominant pathway involves water electrolysis and acidification at the tissue/solution interface. Over the voltage ranges examined in the inventors' previous studies, water and chloride are the main species that undergo redox chemistry.

As shape change comes at the expense of cell injury, the optimization may require identification and selection of the appropriate applied potential (V), duration (t), electrode composition, and needle electrode placement. Combinations of these parameters determine resultant shape change, mechanical stability and tissue viability in a specimen, which are the clinically relevant factors to the reconstructive surgeon. In sum, the present invention may provide the following advantages:

- percutaneous delivery via needle electrodes is less invasive than liposuction technique as there is no need for an incision.
- in situ generation of reactive chemical species; this is not a drug.
- saline solution does not require extensive drug approval for clinical use as it is already approved for human use.
- the process evolves molecular hydrogen and oxygen which serve as endogenous contrast for ultrasound and other imaging technologies.
- simple technology with relatively low cost hardware (needles and power source) and does not require specialists' skills to operate.
- can be performed by physician extenders.
- does not require general anesthesia; local anesthetics will likely be sufficient.
- titratable meaning optimal results can be obtained via multiple low-dose treatments.
- disposable components can be used (lower per use costs).
- treatments can be delivered in an office setting (lower costs incurred).
- minimal downtime for the patient.
- designed for point of care treatments (dermatologists).
- highly localized therapy possible (e.g., under chin, "love handles" arms), which will help achieve better cosmetic outcome.
- treatments can be readily monitored using ultrasonography.
- potential for highly-spatially targeted therapy with high spatial selectivity.
- spatial selectivity is achieved through combination of localization of the electrolytic solution (i.e., saline) and electric field (i.e., needle arrangements).
- may require as few as (1-4 injections) along with simple insertion of a needle applicator (i.e., microneedle patch); thus there will be less physician time involved per treatments.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

It should be understood, of course, that the foregoing relates to exemplary embodiments of the invention and that modifications may be made without departing from the spirit and scope of the invention as set forth in the following claims.

We claim:

1. A method of altering adipose tissue, comprising:
    inserting an electrolytic solution into the adipose tissue;
    creating an electrochemical reaction in the adipose tissue with an anode electrode and a cathode electrode;
    wherein the electrolytic solution is a reagent in the electrochemical reaction in the adipose tissue.

2. The method of claim 1, further comprising providing feedback control of an electronic circuit for creating the electrochemical reaction.

3. The method of claim 2, wherein the electronic circuit is one of a potentiostat and a galvanostat.

4. The method of claim 1, further comprising altering a pH in the adipose tissue.

5. The method of claim 1, further comprising placing at least one of the anode electrode and the cathode electrode in contact with the adipose tissue.

6. The method of claim 5, wherein placing the at least one of the anode electrode and the cathode electrode is in an absence of a voltage gradient across the adipose tissue.

7. The method of claim 1, further comprising disrupting an ionic-bonding network in the adipose tissue.

8. The method of claim 1, further comprising altering the adipose tissue to a physiological pH after creating the electrochemical reaction.

9. The method of claim 1, further comprising injecting the electrolytic solution into the adipose tissue.

10. The method of claim 1, further comprising setting a concentration of electrochemically generated chemical agents, from the anode and cathode electrodes, that affect the adipose tissue, by altering the electrochemical reaction at the anode and cathode electrodes.

11. The method of claim 1, wherein creating the electrochemical reaction includes employing potential-driven electrochemical modification of the adipose tissue (PDEMT).

12. The method of claim 1, further comprising:
identifying and isolating at least one discrete electrochemical reaction that causes at least one of a shape change in the adipose tissue, a change in adipose tissue mechanics, a change in the adipose tissue viability, a change in the adipose tissue matrix structure, and a change in the adipose tissue composition.

13. The method of claim 1, further comprising changing at least one of a physical property and a biological behavior of the adipose tissue.

14. The method of claim 13, wherein:
changing the physical property of the adipose tissue includes mechanical behavior—static or dynamic—electrical behavior, optical property, and/or thermal properties; and
changing the biological behavior of the adipose tissue includes tissue viability, matrix structure, and molecular composition.

15. The method of claim 1, further comprising:
placing the anode and cathode electrodes in a geometric arrangement in the tissue effective for treating or shaping the adipose tissue.

16. A method of altering adipose tissue, comprising:
using at least one of an anodic electrode and a cathodic electrode in the adipose tissue to initiate an electrochemical reaction in the adipose tissue;
adding an electrolytic solution to the adipose tissue as a reagent in the electrochemical reaction;
applying an electrical potential to at least one of the anodic electrode and the cathodic electrode;
whereby an electrical impedance of the adipose tissue is reduced and the electrolyte solution undergoes electrolysis;
whereby the electrochemical reaction alters the adipose tissue.

17. The method of claim 16, wherein the method is carried out in absence of incising the adipose tissue.

18. The method of claim 16, further comprising injecting the electrolytic solution into the adipose tissue prior to applying the electrical potential.

19. The method of claim 16, further comprising injecting the electrolytic solution into the adipose tissue while applying the electrical potential.

20. The method of claim 16, wherein the electrolytic solution is saline.

21. The method of claim 16, wherein the electrolytic solution includes an amphiphilic compound.

22. The method of claim 16, further comprising hydrolyzing the adipose tissue.

23. The method of claim 16, further comprising disrupting cell membranes of the adipose tissue.

24. A method of altering adipose tissue, comprising:
mechanically disrupting the adipose tissue; and
electrochemically degrading the adipose tissue with an electrical potential applied to an anodic electrode and a cathodic electrode while in presence of an electrolytic solution used as a reagent which undergoes electrolysis during the electrochemically degrading.

25. The method of claim 24, wherein mechanically disrupting includes inserting the anodic and cathodic electrodes into the adipose tissue.

26. A method of altering adipose tissue, comprising:
electrochemically generating sodium hydroxide, hydrogen gas, and either chlorine gas or oxygen gas in the adipose tissue by applying an electrical potential to an anode-cathode pair and electrolyzing an electrolytic solution in the adipose tissue; and
electrochemically forming acid/base species in the adipose tissue, which forming alters the adipose tissue;
wherein applying the electrical potential is at a voltage not greater than 5V.

* * * * *